United States Patent
Menon et al.

(10) Patent No.: US 9,996,168 B2
(45) Date of Patent: Jun. 12, 2018

(54) WEARABLE WIRELESS TONGUE CONTROLLED DEVICES

(71) Applicants: K. A. Unnikrishnan Menon, Kollam (IN); Revathy Jayaram, Kollam (IN); Divya Pullarkatt, Kollam (IN); Maneesha Vinodini Ramesh, Kollam (IN)

(72) Inventors: K. A. Unnikrishnan Menon, Kollam (IN); Revathy Jayaram, Kollam (IN); Divya Pullarkatt, Kollam (IN); Maneesha Vinodini Ramesh, Kollam (IN)

(73) Assignee: Amerita Vishwa Vidyapeetham, Kollam, Kerala (IN)

( * ) Notice: Subject to any disclaimer, the term of this patent is extended or adjusted under 35 U.S.C. 154(b) by 34 days.

(21) Appl. No.: 14/690,266

(22) Filed: Apr. 17, 2015

(65) Prior Publication Data
US 2015/0301619 A1 Oct. 22, 2015

(30) Foreign Application Priority Data

Apr. 17, 2014 (IN) .......................... 1990/CHE/2014

(51) Int. Cl.
| | |
|---|---|
| G09G 5/00 | (2006.01) |
| G06F 3/03 | (2006.01) |
| A61F 4/00 | (2006.01) |
| G06F 3/01 | (2006.01) |

(52) U.S. Cl.
CPC .............. G06F 3/0304 (2013.01); A61F 4/00 (2013.01); G06F 3/011 (2013.01)

(58) Field of Classification Search
None
See application file for complete search history.

(56) References Cited

U.S. PATENT DOCUMENTS

| | | | |
|---|---|---|---|
| 7,259,748 B2 | 8/2007 | Ullman et al. | |
| 8,537,036 B2 | 9/2013 | Brusell et al. | |
| 2004/0148174 A1* | 7/2004 | Ullman | G06F 3/011 |
| | | | 704/275 |
| 2005/0033571 A1* | 2/2005 | Huang | G10L 15/20 |
| | | | 704/231 |

FOREIGN PATENT DOCUMENTS

WO  WO 2011002403  *  1/2011  ............. G06F 3/042

* cited by examiner

*Primary Examiner* — Ifedayo Iluyomade
(74) *Attorney, Agent, or Firm* — Convergence Intellectual Property Law P.C.; Jonathan Garfinkel

(57) ABSTRACT

A wearable device and a system to provide an input for a computing device are disclosed. The device comprises a sensing unit to deliver infrared signals to the facial region of a user and to receive transmitted or reflected signals therefrom, and a processing unit to determine the position or movement of the tongue of the user based on the received infrared signals. The processing unit is configured to provide an input to a computing device based on the determined position or movement of the tongue. The system further comprises a transmitter for wirelessly transmitting the input from the processing unit to the computing device.

15 Claims, 8 Drawing Sheets

WEARABLE WIRELESS TONGUE CONTROLLED DEVICES

CROSS-REFERENCE TO RELATED APPLICATIONS

This application claims priority to Indian patent application No. 1990/CHE/2014 entitled WEARABLE WIRELESS TONGUE CONTROLLED DEVICES filed on Apr. 17, 2014, the full disclosures of which are incorporated herein by reference.

DESCRIPTION OF THE RELATED ART

People who are partially or completely paralyzed are unable to use their lower limbs or even all four limbs, mainly due to stroke or trauma to the nervous system because of brain and spinal cord injuries. The number of people suffering from paralysis globally is increasing every year. Approximately, 5.6 million of the American population suffers from paralysis, of which 1.275 million are due to spinal cord injuries. A paralyzed person has to depend on others for carrying out their daily life tasks, which makes their life miserable. With the aid of assistive devices, a disabled person can have a more private and easier life by eliminating or reducing the need for a caretaker.

Recently, assistive devices based on a range of new technologies have been developed to help the disabled in various activities such as mobility, hearing, vision, self-care, safety, etc., thereby enabling them to perform their daily life tasks on their own without depending on caretakers. While designing an assistive device for disabled people, certain factors such as comfort, user preference, reliability, usability and cost should be taken into consideration. One of the main areas in assistive technology is the brain-computer interface (BCI), where electroencephalography (EEG) signals are used to discern a user's intention to carry out a task. However, BCI technology requires high concentration, consumes high set up time, and is not economical. Eye-controlled assistive devices work through sensing eye movement by using cameras and electrooculographic (EOG) measurement. However, the technology requires high user concentration in order to control the device.

The tongue is an organ not influenced by other parts of the body as it is controlled by a cranial nerve. The movement of the tongue is usually not as affected by spinal cord injuries and is minimally affected in case of nervous system damage. The tongue can easily be moved and used for recognizing a user's intention. Hence, much research work has been conducted on tongue-controlled assistive devices. There have been many methods to interface the tongue, including electrical contacts, induction coils, magnetic sensors, etc. U.S. Pat. No. 7,259,748 discloses an apparatus and a method for controlling a cursor on an electronic viewing screen by tongue movements based on ultrasonic signals reflected against the user's tongue and/or mouth cavity. Other devices require magnetic sensors permanently attached to the outside of the mouth or a magnet pierced to the tongue such as U.S. Pat. No. 8,537,036, Huo et al (2008) or Kim et al (2012).

The existing tongue controlled assistive devices have the disadvantage of being invasive. The present disclosure addresses the drawbacks of conventional devices and solves the major constraint of user comfort and ease by designing and developing a device that is non-invasive and unobtrusive, with further related advantages as set forth here.

SUMMARY OF THE INVENTION

Wearable devices and systems for controlling an element displayed on electronic devices are disclosed.

In one embodiment the device comprises a wearable housing comprising at least one sensing unit configured to deliver infrared signals to a facial region of a user and to receive infrared signals therefrom. Each sensing unit comprises at least one infrared emitter and a sensor configured to detect the received infrared signals, and a processing unit configured to analyze the detected infrared signals from the at least one sensing unit and determine the position of the tongue of the user based on the received infrared signals. The processing unit is configured to provide an input to a computing device based on the determined position of the tongue. The device in one embodiment comprises a sensing unit with an infrared transmitter and an infrared receiver packed together. In various embodiments the received infrared signals detected by the sensing units are either transmitted infrared signals or reflected infrared signals. In some embodiments the processing unit comprises a microprocessor for converting the sensor output to computer-readable instruction, and a transmitter for transmitting the computer-readable instruction to an electronic device. The transmitter within the processing unit is configured to transmit the computer readable instruction to the electronic device using a wireless communication protocol selected from one of radio frequency, Bluetooth, Zigbee, Ultra Wide Band or Wi-Fi. In one embodiment of the wearable device the input is configured to control of an on-screen element such as a scrolling command, a steering motion, a movement instruction of an actuator, a page advancement instruction or a click command.

A system for non-contact sensing of the position of a user's tongue and enabling a user to control an electronic device is disclosed, comprising a set of infrared sensing units positioned near a user's face to transmit and receive position information regarding a user's tongue, the sensing units comprising at least one infrared emitter and an infrared sensor. The system further comprises a processing unit with a microprocessor, a memory and a transmitter, the microprocessor configured to receive signals from the sensors comprising position information of the user's tongue and transform the position information to computer-readable instruction. The memory is configured to store code comprising instructions readable by the microprocessor, and the position information received from the sensors, and the transmitter is configured to convey the computer-readable instruction to the electronic device to control the device. In various embodiments of the system conveying the computer readable instruction to the electronic device uses a wireless communication protocol selected from radio frequency, Bluetooth, Zigbee, Ultra Wide Band or Wi-Fi. The computer readable instruction in various embodiments may comprise at least one of a scrolling command, a steering motion, a movement instruction of an actuator, a page advancement instruction or a click command.

Other advantages and aspects of this invention will become apparent upon making reference to the specification, claims, and drawings to follow.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Figure 1A:
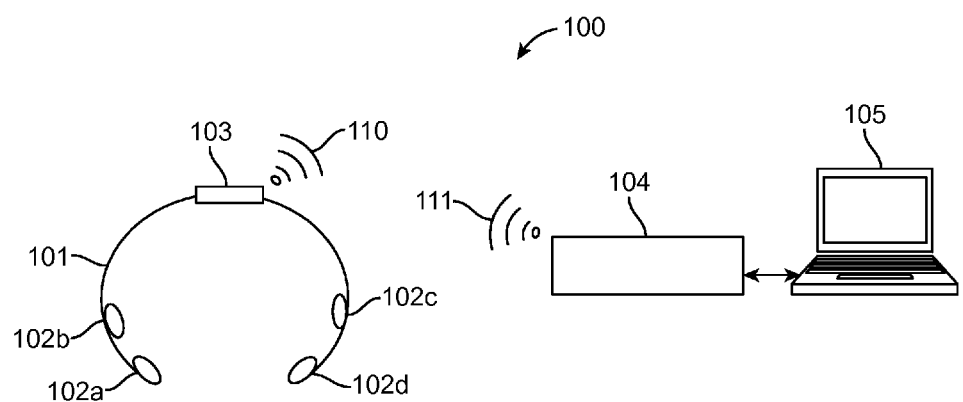
FIG. 1A illustrates one embodiment of a wearable device.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

In some aspects, the present disclosure relates to wearable control devices and systems. Specifically, the present disclosure contemplates wearable control devices configured to provide an input to a computing device by non-contact sensing of the position of a portion of a user's body.

In some aspects, the wearable control device of the present disclosure describes devices, systems, and methods configured to effectively receive one or more user inputs via tongue movements. Embodiments of the present disclosure enable the user to control electronic or mechanical or computing devices such as a computing system including a personal computer or a Smartphone. Embodiments of the present disclosure is further configured to be capable of operating any electrically controlled devices in their environment such as wheel chairs, appliances, etc.

In one embodiment, the wearable control device of the present disclosure comprises a sensing unit and a processing unit disposed within, or coupled with a wearable housing unit. In some aspects, the sensing unit comprises one or more reflective sensors. In some aspects, the reflective sensors comprise an infrared transmitter and an infrared receiver packed together.

As shown in FIG. 1A, one embodiment of a control device 100 comprises a housing unit 101 that is configured as a wearable headset and a plurality of optical sensing units 102a, 102b, 102c, and 102d, such as infrared sensors. In some aspects, the sensing units are distributed on the housing unit 101 such that at least one of the sensing units are positioned on both sides of a user's face.

In some aspects, use of the optical sensors has many advantages over conventional types of sensors such as greater sensitivity and freedom from electromagnetic interference. In some aspects, the movement of the tongue is sensed by variation in the intensity of infrared rays, which is then converted into user commands by a signal processing unit. These commands are transmitted to an electronic device such as a personal computer (PC) or Smartphone.

In one embodiment the sensing units 102a and 102b are positioned on the left hand side of a user's face and 102c, 102d on the right hand side of a user's face. A processing unit 103, in one aspect, is disposed on the head set. In one aspect, the processing unit is used to transform information on position of the tongue of the user into a computer input, such as cursor movements. In some embodiments, the processing unit 103 comprises a microprocessor, a memory and a transmitter. In one aspect, the processing unit 103 transmits the computer input, such as a cursor movement, as wireless signal 110 to a computing device 105 via a receiving unit 104.

Figure 1B:
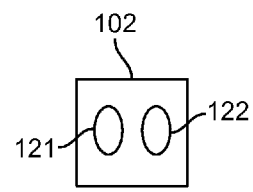
FIG. 1B shows one embodiment of a sensing unit incorporated into the wearable device.

The microprocessor converts the sensor output to computer-readable instructions, and the transmitter transmits the computer-readable instructions to a computing device 105 such as a PC or a smartphone. In some aspects, the control device 100 further comprises a battery unit configured to power the sensing units and the processing unit. As described herein and exemplarily shown in FIG. 1B, in one embodiment, the sensing unit 102 may comprise one or more photodiodes 121 for transmitting the infrared radiation and phototransistor 122 for receiving reflected infrared radiation.

Figure 1C:
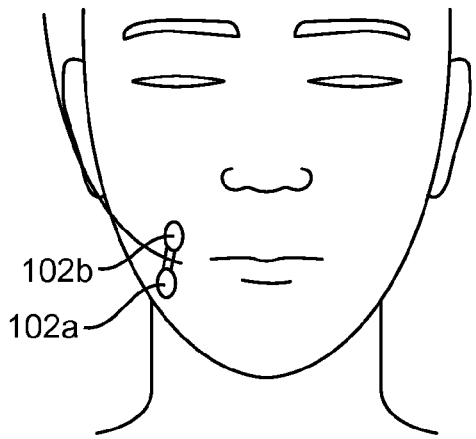
FIG. 1C shows one embodiment of sensing units with reference to a user's facial features
Figure 1D:
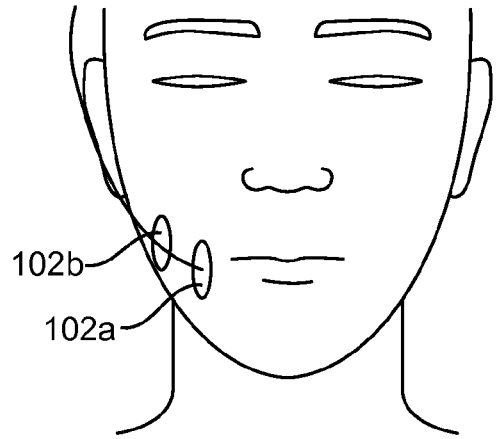
FIG. 1D shows another embodiments of sensing units with reference to a user's facial features.

In one aspect, the infrared sensing units 102 are positioned on the housing unit 101 so that the position of the tongue or the movement of the tongue can be tracked via detected facial muscular movement or contortion as caused by the tongue. In one aspect, the positioning of the sensing units can be customized based on the user's preference i.e., according to where the user can move his/her tongue. In various embodiments alternative configurations of the sensing units with reference to the user's facial features are as shown in FIG. 1C and FIG. 1D. In FIG. 1C the sensing units 102a and 102b are positioned corresponding to the lower and upper jaws, respectively. Alternatively, they could be spaced laterally, as shown in FIG. 1D. In another aspect, the infrared sensing units 102 may be separate from the housing unit 101, wherein the sensing units 102 can be independently placed or attached to a user.

Figure 1E:
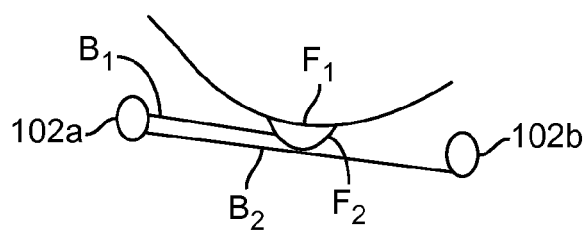
FIG. 1E shows one aspect of detection of tongue position using transmitted and reflected IR beams respectively.
Figure 1F:
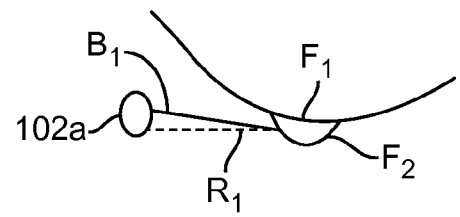
FIG. 1F shows another aspect of detection of tongue position using transmitted and reflected IR beams.

In various embodiments the sensors are configured to detect the position of the facial feature by detecting transmission or reflection of an infrared beam, as shown in FIGS. 1E and 1F. In FIG. 1E, facial features $F_1$ and $F_2$ corresponding to a tongue position are detected by sensors 102a and 102b using transmission or obstruction of the IR beam. For example, beam $B_1$ emitted by sensing unit 102a is obstructed by position of facial feature $F_2$ and does not reach sensor 102b, thereby enabling sensing of tongue position at $F_2$. In position $F_1$, beam $B_2$ passes through unobstructed and tongue position is not detected. This configuration is useful when the facial feature is positioned between two sensors. In another embodiment shown in FIG. 1F, a reflected beam is used to sense the position of the tongue. Sensing unit 102a transmits beam $B_1$ which is reflected as $R_1$ from the facial feature in position $F_2$ and the position of the tongue is therefore detected.

Figure 1G:
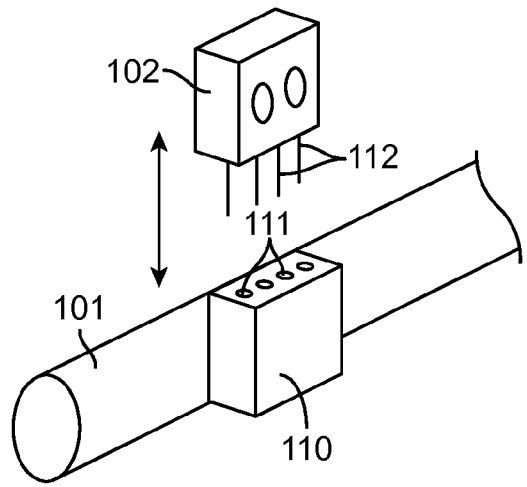
FIG. 1G illustrates one embodiment of a detachable configuration of the sensing unit.

In one aspect, the sensing unit 102 (FIG. 1G) is affixed to housing unit 101 through one or more connection ports 110 with sockets 111 configured to receive pins 112 on the sensing unit 102. The arrangement therefore enables easy connection to and detachment from the housing unit 101. In another aspect, the infrared sensing units are configured of size so that it is easy to mount several sensing units on the housing unit as required by the user. In one aspect the connection ports 110 are provided at various locations such that sensing units 102 can be variably connected in an optimal configuration.

In one embodiment the outputs from various sensing units 102 in FIG. 1A through 1F are taken into account by the control unit 103 to interpret the user command. In one embodiment, computing unit 105 is configured to correlate signals as transmitted by the transmitter with the movement of a computing element such as cursor movement. In another aspect, the computing unit is configured to correlate signals as transmitted by the transmitter with a direct command, e.g., if the sensing unit has detect that the tongue moved from position a to position b, the computing unit may be configured to correlate this movement pattern with the instruction to execute a specific computer instruction. In one aspect the direct command may be a gesture such as used to scroll vertically or horizontally. In one aspect, the direct command may correlate to an action such as a steering motion, a movement instruction of an actuator, a page advancement instruction, a click command such as a left click or a right click command, and so on.

In one embodiment the computing unit 105 comprises a processor and a memory. The memory is configured to store software and programming incorporating suitable algorithms for translating the computer readable instruction into a command as explained earlier, to be executed by the processor. In one embodiment the computing unit 105 can be any computing device such as a personal computer, a handheld device such as a smartphone or a tablet, an embedded computer, a dedicated computer associated with a vehicle or a machine, for example.

In one embodiment the transmission of signals by the control unit 103 in FIG. 1A is configured to use a suitable wireless signal transmission protocol such as radio frequency, Bluetooth, Zigbee, Ultra Wide Band, Wi-Fi etc. to transmit signals to a computing device 105.

In one embodiment, the sensing units are positioned close to the cheek and in view of the high sensitivity of the system, the user does not feel much strain in pushing the cheek to actuate the sensors.

Figure 2A:
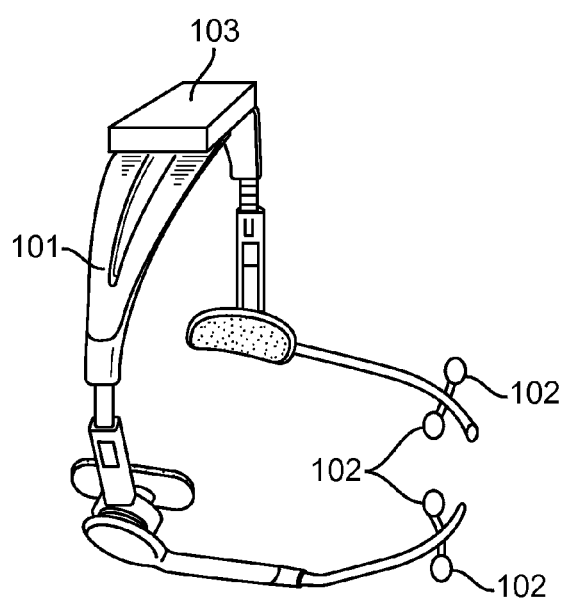
FIG. 2A illustrate one embodiment of of the housing.
Figure 2B:
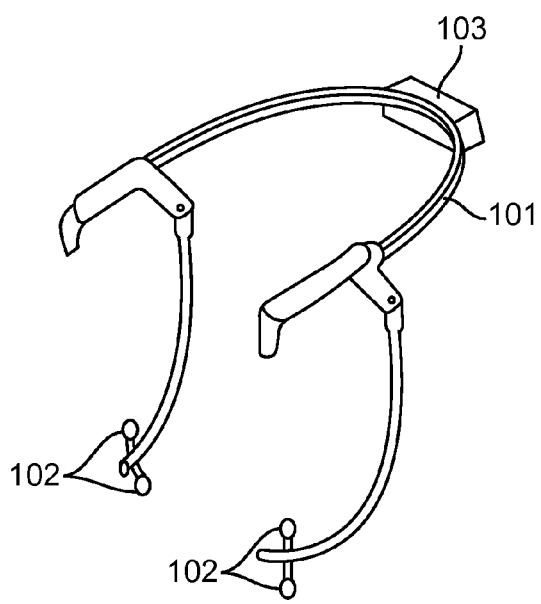
FIG. 2B illustrates another embodiment of the housing.

In one aspect, the housing unit 101 is configured as a wearable band, which is configured to be at least partially surrounding a user's head (skull) either laterally or circumferentially. Such configurations are illustrated in the examples shown in FIG. 2A showing the housing unit 101 going over the top of the head with control unit 103 located on top. Similarly, FIG. 2B illustrates an embodiment where the housing 101 is anchored at the level of the ears and laterally surrounding the user's head, with control unit 103 located at the back. In another aspect, the housing unit 101 may be configured as a cap or a helmet that covers a portion of a user's head. In yet another aspect, the housing unit 101 can be suspended around a portion of a user's head. The housing unit 101 be supported by a scaffold that is connected to another device, e.g., a wheelchair, or in the alterative, the scaffold can be supported by the user's shoulder. In still yet another aspect, the housing unit 101 may be configured to be portable, such that the user may hold the housing unit over a facial area.

In one aspect, the computing unit can be customized to reflect the customization of the sensing units. For example, after the sensing units have been customized or repositioned based on user's preference and/or user's facial features, the computing unit can be calibrated to reflect the new configurations of sensor positions.

Figure 3:
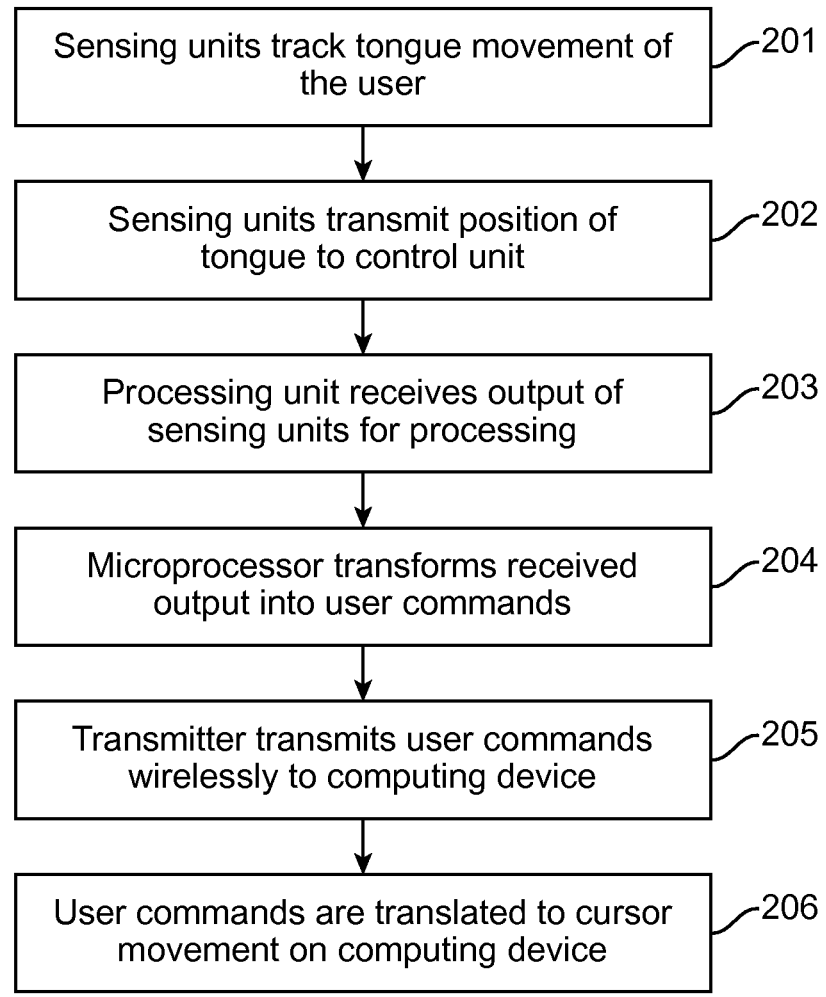
FIG. 3 is a flow chart showing one exemplary functioning of the device.

A flow diagram depicting operation of the device 100 according to one embodiment of the invention is shown in FIG. 3. The sensing units track the tongue movement or the tongue position of the user in step 201 and transmit the movement pattern or position of tongue to the processing unit in step 202. The processing unit receives the output of the sensing units for processing in step 203. In step 204, the microprocessor of the processing unit transforms the received output into user commands and the transmitter of the processing unit transmits the user commands wirelessly to computing device in step 205. In the next step 206, the user commands are then translated to one or more inputs to a computing device.

Figure 4:
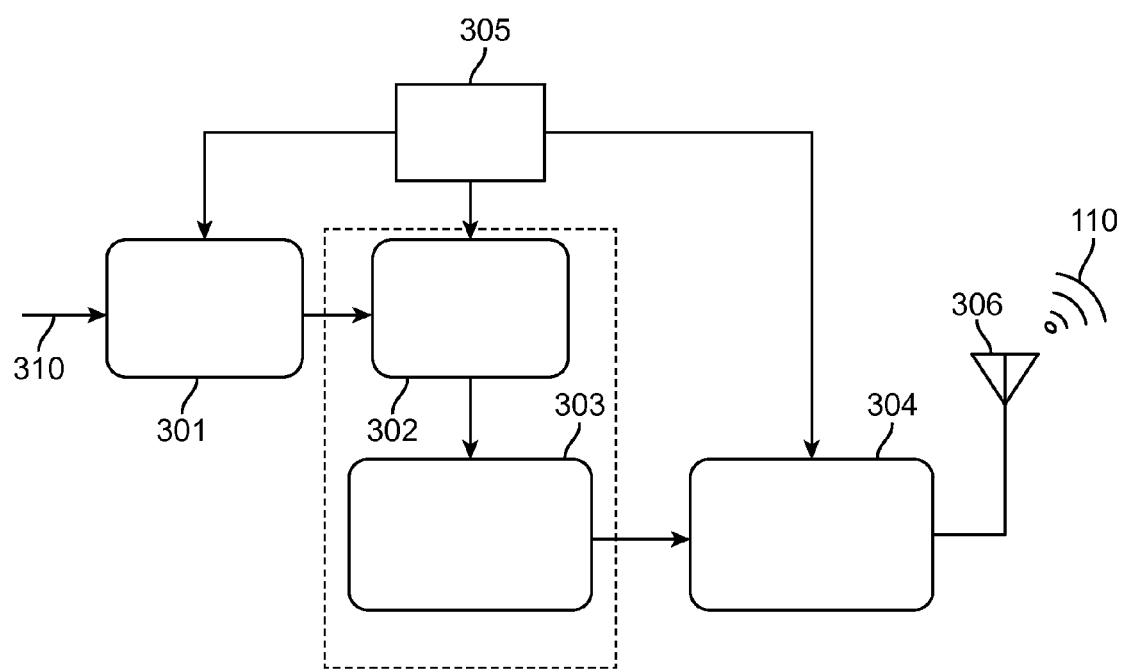
FIG. 4 shows one embodiment of a detailed block diagram of the processing unit.

A block diagram of the processing unit 103 according to one embodiment of the invention shown in FIG. 1A is detailed in FIG. 4. The sensors' output voltages are sent to the processing unit for signal processing. Amplifier 301 is provided in order to amplify the voltage signal, which after amplification, is sent to an analog to digital converter (ADC) 302 for digitizing. According to the digital values obtained, the user commands are generated by the Arithmetic Logic Unit (ALU) 303. The processing unit is powered by a battery 305 which could be a non-rechargeable battery or a rechargeable type charged using a convenient interface such as a USB interface. A comparison algorithm is used for command generation.

Various user commands are created using four sensors, as further illustrated. These commands are then provided to module 304 for wireless transmission. These transmitted commands are then received by a wireless receiver (104) which is connected to the computing device (105) such as PC or Smartphone and moves the cursor accordingly. As already stated with reference to FIG. 1A, the wireless signal transmission protocol is any suitable protocol such as radio frequency, Bluetooth, Zigbee, Ultra Wide Band, Wi-Fi, etc. Thus, the user can control a computing device, through which any device can be controlled.

Figure 5A:
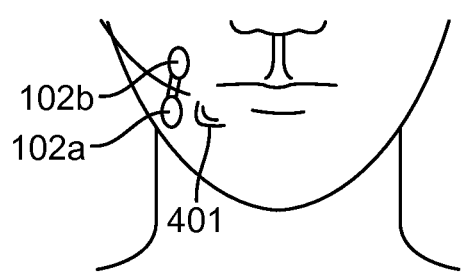
FIG. 5A illustrates an exemplary command generated using tongue position and movement according to embodiments of the invention.
Figure 5B:
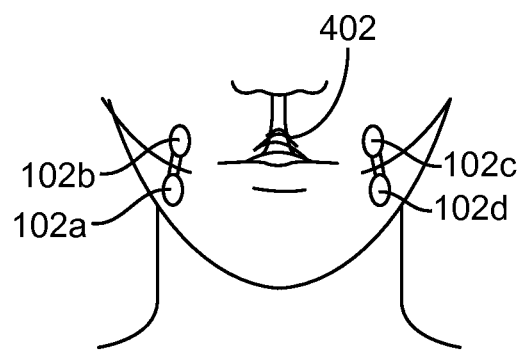
FIG. 5B illustrates an exemplary command generated using tongue position and movement according to embodiments of the invention.

Various embodiments of user commands generated using tongue positioning and movement according to the invention are illustrated in FIG. 5A to 5D. The position of the sensors in the housing 101 with respect to each cheek and the corresponding user commands generated are given in Table I. In one embodiment shown in FIG. 5A, positioning the tongue at location 401 at the lower right hand corner is captured by sensors 102a and 102b and signals the cursor to move right, as shown in Table I. Other cursor positions are similarly performed as further illustrated in Table I. In one embodiment a "click" function can be performed by positioning the tongue in the middle such that all four sensors 102a to 102d capture the signal, corresponding to position 402 as shown in FIG. 5B.

Figure 5C:
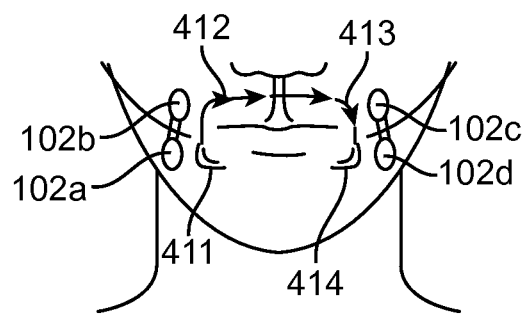
FIG. 5C illustrates an exemplary command generated using tongue position and movement according to embodiments of the invention.
Figure 5D:
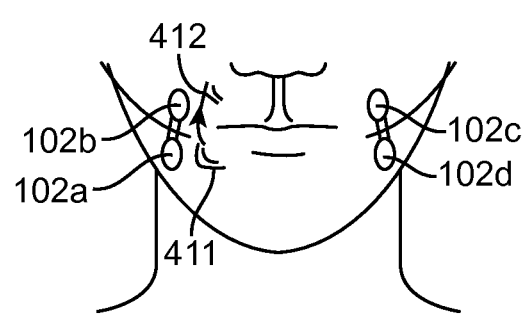
FIG. 5D illustrates an exemplary command generated using tongue position and movement according to embodiments of the invention.

In various embodiments of the invention the direct functional commands may correspond to movement of the tongue in a sequence as illustrated in Table 2 and in FIGS. 5C and 5D. In one embodiment shown in FIG. 5C, the sequence of commands through positions 411, 412, 413 and 414 corresponding to "left click" command is illustrated. In one embodiment in FIG. 5D, a "scroll up" command is illustrated, as the tongue is moved from position 411 to 412.

TABLE I

User Commands Corresponding to Sensor Position

| Sensor Position | User Commands | Cursor Movements |
|---|---|---|
| Right Bottom (RB) | R | Right |
| Right Top (RT) | U | Up |
| Left Bottom (LB) | L | Left |
| Left Top (LT) | D | Down |
| All Sensors | C | Click |

TABLE II

User Commands Corresponding to Sensed Movement

| Tongue Movement | Sensor Position | User Commands |
|---|---|---|
| Top ⇔ Bottom | RB ⇔ RT or LB ⇔ LT | Scroll UP/DOWN |
| Left ⇔ Right | LT ⇔ RT or LB ⇔ RB | Scroll LEFT/RIGHT |
| Circular - Left | RB - RT - LT - LB | LEFT CLICK |
| Circular - Right | LB - LT - RT - RB | RIGHT CLICK |

It must be noted that the embodiments shown in Table I and II are exemplary or illustrative and are not meant to be exhaustive.

EXAMPLES

Examples of the implementation and use of the device are now illustrated. The algorithm used for command generation is described in detail below. A comparison approach is used for the conversion mechanism, where the values from each sensor are compared with a threshold value. If the value is greater than the threshold value, then the corresponding command is generated and given to the wireless module for transmission. The sensor output voltage is given to the input channels of the microcontroller. Outputs from 'right', 'left', 'up' and 'down' sensors are given to channel 1, 2, 3 and 4, respectively.

The algorithm is implemented in all sensors and shows the code for the 'right' sensor, which becomes the user command a', and also the 'click' action.

Algorithm 1: Algorithm for Generating command 'R' and 'C'

```
1:      START
        Initialization
2.         for all (Time = 10s) do
3.            Valuer = readadc_channel1;
4.         end for
        End Initialization
        Activation
5.         If (Valuer > Threashold_R) then
6.            Send(R);
7.            for all (Time = 5s) do
8.               if (Valuer > Threshold_R) then
9.                  Send(C);
10.              end if
11.           end for
12.        end if
13:     END
```

An initialization phase is provided in order to fix the threshold value. This threshold is not a preset value, but will be fixed in real time. Initially, for the first 10 seconds after the device is placed in position, the tongue should be in resting position so that the threshold value will be continuously read and fixed. After 10 seconds the activation phase begins, where the user can start the tongue action by blocking the particular sensor according to which direction they want to move the cursor. The user will be informed of the start of the activation state by a 'START' command being displayed on the screen. Then the values, generated by blocking each sensor are read from the analog to digital converter (ADC) of the processing unit, and are checked with the threshold value. If the read value is greater than the threshold value it indicates that the sensor is blocked and a corresponding command is send for transmission i.e. if it is from right sensor, a' is send. Now the unit waits for 5 seconds after unblocking of that particular sensor is detected and if again the sensor is blocked i.e. read value is greater than the threshold value, then it is interpreted as click and the command 'C' is transmitted. Thus click function will be performed when blocking the sensor once again after unblocking. Apart from this if the tongue is in resting position for more than 5 minutes then the processing unit will change its state from active to sleep leading to power saving.

Experimental Results

Figure 6:
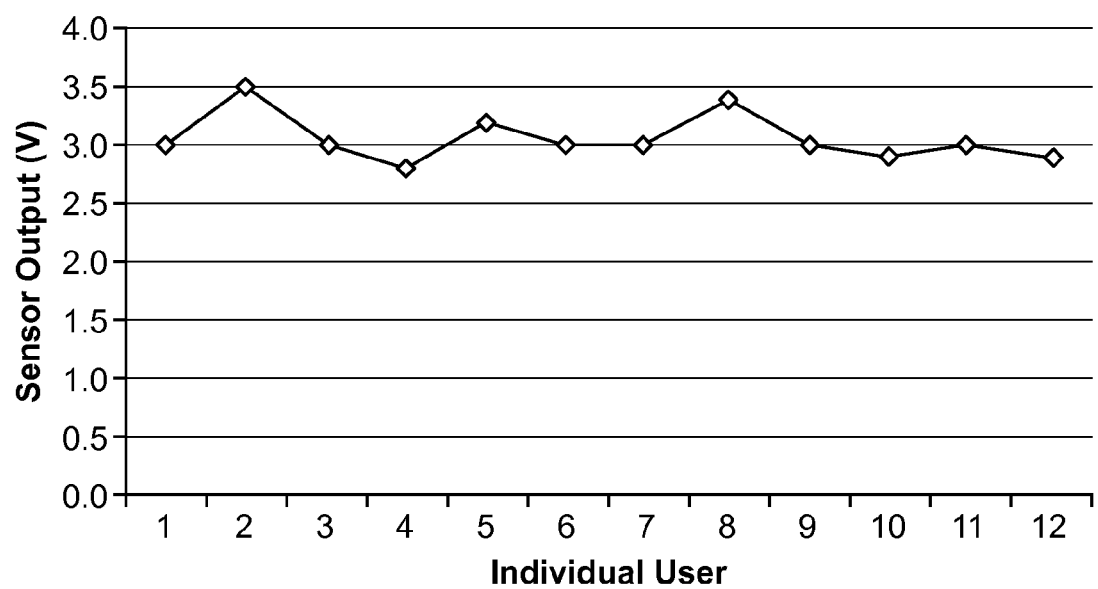
FIG. 6 is an exemplary graph showing experimental results of variation in magnitude of sensor signal with reference to individual users.

A prototype for one aspect of an assistive device of the present disclosure has been developed and was tested on twelve physically able humans. When tongue is in resting position, the sensor values were found to be varying with users having different skin color, texture etc. The variations in magnitude of sensor signal with respect to different people are given in FIG. 6. From FIG. 6, it is understood that different users produced different sensor outputs and the range of values also differ from 3.5 to 2.8 V. This problem was solved with the 10 second initialization phase conducted as soon as the device in place, as discussed in the algorithm section. Even though the voltages of the sensors vary with respect to individuals, the threshold value is fixed after the device is switched on (not preset). This adaptive feature allows the different threshold values for different users and the variation of the sensor output will be with respect to their own individual thresholds, thus providing the necessary adaptive, individual conditions for the command generation.

Figure 7A:
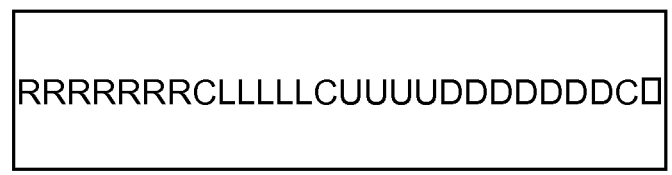
FIG. 7A shows exemplary wireless reception of user commands displayed in serial port terminal of the computing device.

All twelve individual users were successfully used the assistive device of the present disclosure and were able to create all the five user commands. These user commands were generated by users by blocking all four sensors, one by one and are shown in FIG. 7A. These commands were transmitted and captured wirelessly and displayed in the serial port terminal.

Figure 7B:
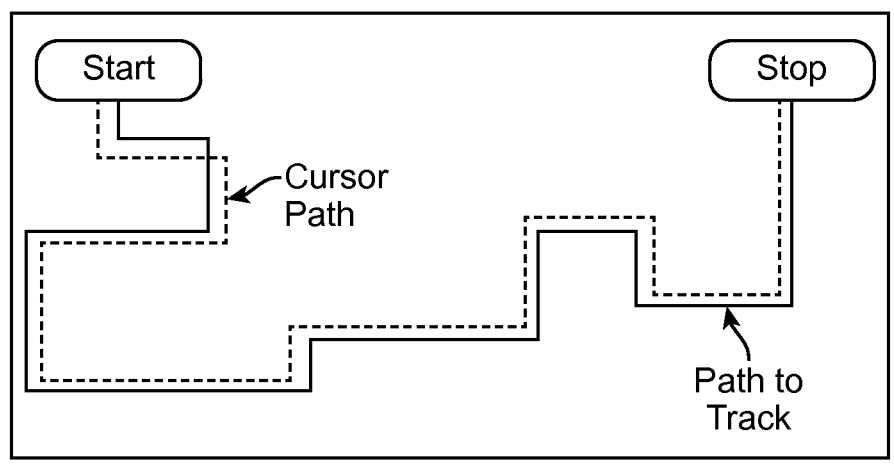
FIG. 7B shows exemplary experimental results of cursor tracking using one embodiment of the device of the invention.

Path Tracking: For analyzing successful cursor movement, a path tracking experiment was conducted, using five individuals. A path was shown to each user, in a PC screen, and they were told to track/follow the path by moving the cursor using the assistive device of the present disclosure. An example of tracking is shown in FIG. 7B where the target path and actual path of the cursor are traced. In a second trial, a user was able to type using an on-screen keyboard.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A wearable device, comprising: a wearable housing comprising a first sensing unit; a second sensing unit; wherein the first and second sensing units are configured to directly deliver infrared signals to the other sensing unit and to receive a transmission of said signals from the other sensing unit; wherein the device is configured to detect transmission of the signals between the sensing units; and wherein the device is configured to detect obstruction of the signals between the sensing units by cheek or lip caused by a tongue pushing on the cheek or lip within a mouth; and a processing unit configured to analyze the detected infrared signals from the first and the second sensing units and determine a position of the tongue of the user within the mouth based on detection of transmission of the signals between the sensing units and obstruction of the signals between the sensing units; wherein the processing unit is configured to provide an input to a computing device based on the determined position of the tongue within the mouth.

2. The wearable device of claim 1, wherein the sensing unit comprises an infrared transmitter and an infrared receiver packed together.

3. The wearable device of claim 1, wherein the processing unit comprises a microprocessor for converting the sensor output to computer-readable instruction, and a transmitter for transmitting the computer-readable instruction to an electronic device.

4. The wearable device of claim 3, wherein the transmitter is configured to transmit the computer readable instruction to the electronic device using a wireless communication protocol selected from radio frequency, Bluetooth, Zigbee, Ultra Wide Band or Wi-Fi.

5. The wearable device of claim 1, wherein the input is configured to control an on-screen element.

6. The wearable device of claim 5, wherein the on-screen element comprises at least one of a scrolling command, a steering motion, a movement instruction of an actuator, a page advancement instruction or a click command.

7. The wearable device of claim 1, wherein the device is configured to detect obstruction of the signals between the sensing units by facial muscular movement or contortion as caused by the tongue within the mouth.

8. A system for non-contact sensing of the position of a user's tongue within a mouth, comprising: a first and second infrared sensing units configured to transmit position information regarding a user's tongue within the mouth; wherein the first and second sensing units each comprise at least one infrared emitter and at least one infrared sensor; and wherein the first and second sensing units are configured to directly deliver infrared signals to the other sensing unit and to receive a transmission of said signals from the other sensing unit; wherein the sensing units are configured to detect transmission of the signals between the sensing units; and wherein the system is configured to detect obstruction of the signals between the sensing units by cheek or lip caused by a tongue pushing on the cheek or lip within the mouth; and a processing unit comprising a microprocessor, a memory and a transmitter, wherein: the microprocessor is configured to receive signals from the sensing units comprising position information of the user's tongue within the mouth, wherein the microprocessor is configured to analyze the signals from the sensing units and determine a position of the tongue of the user within the mouth based on detection of transmission of the signals between the sensing units and obstruction of the signals between the sensing units; and wherein the microprocessor is further configured to determine a computer-readable instruction based on the determined position of the tongue within the mouth; the memory is configured to store code comprising instructions readable by the microprocessor, and the position information received from the sensing units; and the transmitter is configured to transmit the computer-readable instruction.

9. The system of claim 8, wherein conveying the computer readable instruction to the electronic device uses a wireless communication protocol selected from radio frequency, Bluetooth, Zigbee, Ultra Wide Band or Wi-Fi.

10. The system of claim 8, wherein the computer readable instruction comprises at least one of a scrolling command, a steering motion, a movement instruction of an actuator, a page advancement instruction or a click command.

11. The system of claim 8, wherein the system is configured to detect obstruction of the signals between the sensing units by facial muscular movement or contortion as caused by the tongue within the mouth.

12. The device of claim 5, wherein the input is determined based on movement of the tongue within the mouth.

13. The system of claim 10, wherein the computer readable instruction is determined based on movement of the tongue within the mouth.

14. The device of claim 1, wherein the device is configured to indirectly detect the position of the tongue while the tongue is wholly within the mouth by detecting obstruction of the signals between the sensing units by cheek or lip positions corresponding to tongue positions within the mouth.

15. The system of claim 8, wherein the system is configured to indirectly detect the position of the tongue while the tongue is wholly within the mouth by detecting obstruction of the signals between the sensing units by cheek or lip positions corresponding to tongue positions within the mouth.

* * * * *

UNITED STATES PATENT AND TRADEMARK OFFICE
CERTIFICATE OF CORRECTION

PATENT NO. : 9,996,168 B2  
APPLICATION NO. : 14/690266  
DATED : June 12, 2018  
INVENTOR(S) : Menon et al.

Page 1 of 1

It is certified that error appears in the above-identified patent and that said Letters Patent is hereby corrected as shown below:

On the Title Page

In item: (73), Line(s): 1, Assignee:
"Amerita Vishwa Vidyapeetham," to read as --Amrita Vishwa Vidyapeetham,--

Signed and Sealed this
First Day of January, 2019

Andrei Iancu
*Director of the United States Patent and Trademark Office*